(12) United States Patent
Yanai et al.

(10) Patent No.: US 6,316,406 B1
(45) Date of Patent: Nov. 13, 2001

(54) DEPSIPEPTIDES CONTAINING N-SUBSTITUTED GLYCINE RESIDUE

(75) Inventors: Makoto Yanai; Masashi Suzuki; Norio Oshida; Koji Kawamura; Shigeru Hiramoto; Orie Yasuda; Nobuhiro Kinoshita; Akiko Shingai; Masako Takasu, all of Saitama-ken (JP)

(73) Assignee: Nisshin Seifun Group Inc., Tokyo (JP)

( * ) Notice: Subject to any disclaimer, the term of this patent is extended or adjusted under 35 U.S.C. 154(b) by 0 days.

(21) Appl. No.: 09/379,614

(22) Filed: Aug. 24, 1999

Related U.S. Application Data

(62) Division of application No. 09/218,125, filed on Dec. 21, 1998, now Pat. No. 6,001,815.

(30) Foreign Application Priority Data

Dec. 25, 1997 (JP) .................................................. 9-357766

(51) Int. Cl.⁷ .............................. A61K 38/15; C07K 7/00
(52) U.S. Cl. ............................................ 514/11; 530/323
(58) Field of Search ......................... 514/9, 11; 530/317, 530/321, 323

(56) References Cited

U.S. PATENT DOCUMENTS

| | | | | |
|---|---|---|---|---|
| 4,582,639 | * | 4/1986 | Matson et al. ....................... | 530/331 |
| 5,801,143 | * | 9/1998 | Hiramoto et al. ....................... | 514/9 |
| 6,001,815 | * | 12/1999 | Yanai et al. ............................. | 514/18 |
| 6,211,145 | * | 4/2001 | Yanai et al. ............................. | 514/10 |

OTHER PUBLICATIONS

Ignatius et al. Expression of Apolipoprotein E During Nerve . . . PNAS USA, vol. 83, pp. 1125–1129, Feb. 1986.*
Yamada et al. Increased clearance of plasma cholesterol . . . PNAS USA. vol. 86, pp. 665–669, Jan. 1989.*
Shimano et al. Plasma Lipoprotein Metabolism . . . J. Clin. Invest. vol. 90, pp. 2084–2091, Nov. 1992.*
T. Ohshima, et al., Peptide Chemistry, pp. 33–36, "A New Endothelin Antagonist Lipopeptide Isolated from the Strain of *Bacillus Subtilis*", 1995.
R. J. Simon, et al., Proc. Natl. Acad. Sci. USA, vol. 89, pp. 9367–9371, "Peptoids: A Modular Approach to Drug Discovery", Oct., 1992.

* cited by examiner

*Primary Examiner*—Jeffrey E. Russel
(74) *Attorney, Agent, or Firm*—Oblon, Spivak, McClelland & Neustadt, P.C.

(57) ABSTRACT

A depsipeptide containing N-substituted glycine residue having the formula (1) or (2):

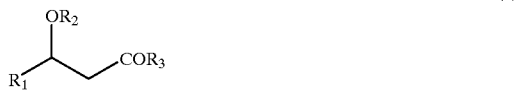

(1)

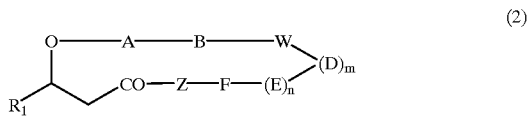

(2)

(wherein $R_1$ is a straight or branched alkyl group of 5–20 carbon atoms or a straight or branched alkoxymethyl group of 5–15 carbon atoms; $R_2$ is a group of the formula —A—B—W—$(D)_m$—$(E)_n$, —A—B—W—$(D)_m$—$(E)_n$—F or —A—B—W—$(D)_m$—$(E)_n$—F—Z; $R_3$ is a hydroxyl group, a lower alkoxy group, a benzyloxy group, or a group of the formula —Z, —Z—G or —Z—G—J; A, B, D, E, F, G and J independently are an N-substituted glycine residue or a residue of an amino acid selected from the group consisting of alanine, valine, leucine, serine, etc.; W and Z independently are a residue of an amino acid selected from the group consisting of an aspartic acid, a glutamic acid, etc.; at least one of A, B, D, E, F, G and J is an N-substituted glycine residue) or a pharmacologically acceptable salt thereof. The above depsipeptides have a promoting activity on the production of apolipoprotein E, and are useful as a therapeutic agent for neurologic damages, especially dementia, and hyperlipemia.

9 Claims, No Drawings

DEPSIPEPTIDES CONTAINING N-SUBSTITUTED GLYCINE RESIDUE

This application is a divisional of prior U.S. application Ser. No. 09/218,125, filed Dec. 21, 1998, (now U.S. Pat. No. 6,001,815).

BACKGROUND OF THE INVENTION

1. Field of the Invention

This invention relates to a novel depsipeptide containing N-substituted glycine residue and a pharmaceutical composition containing the same as an active ingredient. The depsipeptides of the invention have a promoting activity on the production of apolipoprotein E and are useful as therapeutic agents for neurologic damages, especially dementia, and hyperlipemia.

2. Description of the Prior Art

As a therapeutic agent for senile dementia, there have been mainly applied activators of cerebral circulation and metabolism, but these drugs have no improving effect on disintegration of the central nervous system which is believed to cause senile dementia. Consequently, they do not show any improving effect on dysmnesia or acalculia which is said to be the main symptom of dementia. In view of this, there has been desired a drug as a new type of the therapeutic agent for senile dementia which may promote the repair and growth of nervous systems while inhibiting the disintegration of the central nervous system. On the other hand, it has been reported that apolipoprotein E may be generated at a high level at the damaged sites of nervous systems which are being repaired (For example, refer to M. J. Igunatius et al., Proc. Natl. Acad. Sci. U.S.A., 83, 1125 (1986)). This suggests that apolipoprotein E will play an important role in repairing the damaged nervous systems.

Moreover, it has recently been reported that a remarkable reduction in a plasma cholesterol level can be observed when apolipoprotein E is administered intravenously to WHHL rabbit, which is a model animal for human familial hypercholesterolemia homozygote (Yamada et al., Proceeding of National Academy Science USA, Vol. 86, pp. 665–669, 1989). Also, it has been reported that plasma cholesterol and plasma triglyceride can be noticeably decreased by transducing a gene for apolipoprotein E into the mouse liver and expressing apolipoprotein E in a large mass (Shimano, H. et al., Journal of Clinical Investigation, Vol. 90, pp. 2084–2091, 1992).

As is apparent from these reports, the increase in plasma apolipoprotein E concentration has been regarded as extremely effective in the treatment of hyperlipemia, especially familial hypercholesterolemia homozygote which has been hitherto considered as difficult to be treated with the prior art drugs.

DETAILED DESCRIPTION OF THE INVENTION

In view of the foregoing, there has been desired a novel type of an antidementia agent which may promote the repairing and growth of the nervous systems and inhibit the disintegration of the central nervous system. It may be inferred that such a desire would be accomplished by compounds promoting the production of apolipoprotein E.

Also, it has been desired to research and develop a drug which may increase a plasma apolipoprotein E concentration as a therapeutic method for hyperlipemia, especially familial hypercholesterolemia homozygote which has been hitherto considered as difficult to be treated with the prior art drugs.

Under these circumstances, we have made our earnest studies to provide a drug for promoting the production of apolipoprotein E, and as a result, the depsipeptides having a specific structure may possess such activities, upon which this invention has been completed.

The present invention relates to a depsipeptide containing N-substituted glycine residue having the formula (1) or (2):

(1)

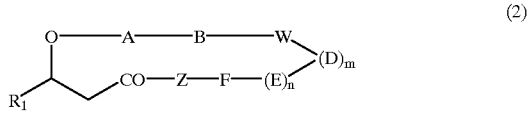

(2)

wherein $R_1$ is a straight or branched alkyl group of 5–20 carbon atoms or a straight or branched alkoxymethyl group of 5–15 carbon atoms;

$R_2$ is a group of the formula —A—B—W—(D)$_m$—(E)$_n$, —A—B—W—(D)$_m$—(E)$_n$—F or —A—B—W—(D)$_m$—(E)$_n$—F—Z;

$R_3$ is a hydroxyl group, a $C_1$–$C_6$ alkoxy group, a benzyloxy group, or a group of the formula —Z, —Z—G or —Z—G—J;

A, B, D, E, F, G and J independently are a N-substituted glycine residue having the formula (3)

(3)

(in which $R_4$ is an alkylene group of 1–4 carbon atoms and $R_5$ is a hydrogen atom, a hydroxy group, a carboxy group or a carbamido group) or a residue of an amino acid selected from the group consisting of alanine, valine, leucine, isoleucine, serine, threonine, lysine, hydroxylysine, arginine, cysteine, methionine, phenylalanine, tyrosine, tryptophan, histidine, proline, 4-hydroxyproline, piperidine-4-carboxylic acid, homoproline, octahydroindole-2-carboxylic acid, norvaline, norleucine, α-t-butylglycine, cyclohexylglycine, azetidine-2-carboxylic acid, 3-(3-pyridyl)alanine, (3-N-methyl)piperidylalanine, 3-(2-naphthyl)alanine, β-cyclohexylalanine, β-t-butylalanine, 9-anthracenylalanine, α-methylalanine, 2-aminobutanoic acid, aspartic acid, asparagine, glutamic acid and glutamine which is optionally substituted with an N-($C_1$–$C_4$) alkyl;

W is a residue of an amino acid selected from the group consisting of aspartic acid, glutamic acid and an amino acid of the formula (4)

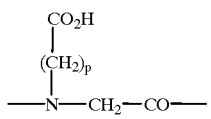

(wherein p is an integer of 1–4);

Z is a residue of an amino acid selected from the group consisting of aspartic acid, asparagine, glutamic acid, glutamine, alanine, serine and lysine or the N-substituted glycine residue of the formula (3); m and n are independently 0 or 1; provided that a free amino group, a free carboxy group, a free hydroxy group, a free mercapto group or a free ω-carbamido group and/or a N-terminal amino group possibly existing in said amino acid residues for the above A, B, D, E, F, G, J, W and Z may be protected by a group commonly used as a protecting group in peptide chemistry, and when A, B, D, E, F, G, J, W and Z are a residue of lysine, hydroxylysine, glutamic acid or aspartic acid, either α- or ω-amino or carboxyl group existing in said residue may form a peptide linkage with its adjacent amino acid and at least one of A, B, D, E, F, G, J, W and Z is the N-substituted glycine residue of the formula (3), or a pharmacologically acceptable salt thereof.

Especially the present invention relates to a depsipeptide of the formula (1) or (2) wherein A, B, D, E, F, G and J independently are the N-substituted glycine residue of the formula (3) or a residue of an amino acid selected from the group of alanine, valine, leucine, isoleucine, phenylalanine, tyrosine, proline, β-t-butylalanine and aspartic acid; W is a residue of an amino acid selected from the group consisting of aspartic acid, glutamic acid and the amino acid of the formula (4); Z is a residue of an amino acid selected from the group consisting of aspartic acid, asparagine, glutamic acid, glutamine, alanine, serine and lysine or the N-substituted glycine residue of the formula (3) and at least one of A, B, D, E, F, G, J and W is the N-substituted glycine residue of the formula (3); and m and n are 1, or a pharmacologically acceptable salt thereof.

Preferable compounds of the formula (1) are the depsipeptides wherein A is an N-($C_1$–$C_4$) alkylglycine residue of the formula (3); B is a residue of an amino acid selected from the group consisting of leucine, isoleucine, phenylalanine, β-t-butylalanine and aspartic acid; D is a residue of an amino acid selected from the group consisting of valine, phenylalanine, alanine and aspartic acid; E, F, G and J are each independently residues of an amino acid selected from the group consisting of leucine, isoleucine and alanine; W is a residue of an amino acid selected from the group consisting of aspartic acid, glutamic acid and the amino acid of the formula (4); Z is a residue of an amino acid selected from the group consisting of aspartic acid, glutamic acid, glutamine, asparagine and lysine or the N-substituted glycine residue of the formula (3); and m and n are 1, or a pharmacologically acceptable salt thereof.

More preferable compounds of the invention are the depsipeptides of the formula (1) wherein A is an N-($C_1$–$C_4$) alkylglycine residue of the formula (3); B is an N-($C_1$–$C_4$) alkylglycine residue of the formula (3); D is a residue of an amino acid selected from the group consisting of valine, phenylalanine, alanine and aspartic acid; E, F, G and J are each independently residues of an amino acid selected from the group consisting of leucine, isoleucine and alanine; W is a residue of an amino acid selected from the group consisting of aspartic acid, glutamic acid and the amino acid of the formula (4); Z is a residue of an amino acid selected from the group consisting of aspartic acid, glutamic acid, glutamine, asparagine and lysine or the N-substituted glycine residue of the formula (3); and m and n are 1, or a pharmacologically acceptable salt thereof.

Most preferable compounds of the formula (1) are the depsipeptides wherein A, B, D, E, F, G and J are the N-($C_1$–$C_4$) alkylglycine residue of the formula (3); W is a residue of an amino acid selected from the group consisting of aspartic acid, glutamic acid and the amino acid of the formula (4); Z is a residue of an amino acid selected from the group consisting of aspartic acid, glutamic acid, glutamine, asparagine and lysine or the N-substituted glycine residue of the formula (3); and m and n are 1, or a pharmacologically acceptable salt thereof.

Furthermore, the present invention relates to a pharmaceutical composition which contains as an active ingredient a therapeutically effective amount of the depsipeptide of the formula (1) or (2) and a pharmaceutically acceptable carrier therefor.

The invention especially relates to a pharmaceutical composition for promoting the production of apolipoprotein E which contains as an active ingredient a therapeutically effective amount of the depsipeptide of the formula (1) or (2) and a pharmaceutically acceptable carrier therefor.

The invention further relates to a pharmaceutical composition for treating neurologic damages, dementia or hyperlipemia which contains as an active ingredient a therapeutically effective amount of the depsipeptide of the formula (1) or (2) and a pharmaceutically acceptable carrier therefor.

Further the invention relates to a method for treating neurologic damages, dementia or hyperlipemia which comprises a therapeutically effective amount of the depsipeptide of the formula (1) or (2) to a host affected with neurologic damages, dementia or hyperlipemia.

The invention still further relates to the use of the depsipeptide of the formula (1) or (2) for treating neurologic damages, dementia or hyperlipemia.

In the above formula (1), $R_1$ is preferably a straight alkyl or alkoxymethyl group of 6–12 carbon atoms and $R_3$ is preferably a hydroxyl group.

As an example of the alkenyl group of 1–4 carbon atoms represented by $R_4$, there may be mentioned a methylene, propylene, 1-methyl-ethylene group or butylene group or the like.

The above amino acids of which the depsipeptide of the invention is composed may be in the form of either L-isomer or D-isomer, while the amino acids represented by A, D, F, J, W and Z in the depsipeptide of the above formula (1) or (2) may be preferably L-isomers and the amino acid represented by B and E may be preferably D-isomers.

As the protecting groups which may be applied for protecting a free amino group in the amino acid residue, there may be mentioned, for example, a t-butoxycarbonyl (hereinafter referred to as "Boc") group, a benzyloxycarbonyl group (hereinafter referred to as "Cbz"), a p-methoxybenzyloxycarbonyl group or a 9-fluorenylmethoxycarbonyl (hereinafter referred to as "Fmoc") or the like; a benzyloxy group (hereinafter referred to as "OBzl") or a t-butoxy (hereinafter referred to as "OtBu") or the like as a protecting group for carboxyl group; 4,4'-dimethoxybenzhydryl (hereinafter referred to as "Mbh") group, a trityl group (hereinafter referred to as "Trt") or the like as a protecting group for terminal carbamido group of Gln or Asn.

As the protecting group for a hydroxy group in the amino acid residue, there may be mentioned a OBzl group, a OtBu group, etc., while as the protecting group for a mercapto group, there may be mentioned a benzyl group, a Trt group, an acetamidomethyl group, etc.

As the protecting group for a C-terminal carboxyl group in the above depsipeptide, there may be mentioned a OBzl group, a OtBu group, etc.

The depsipeptides of the invention have a promoting activity on the production of apolipoprotein E in Hep G2 cells having various functions in the liver. Since apolipoprotein E has a repairing action on neurologic damages and further a lowering action on cholesterol and triglyceride levels in the blood, the depsipeptides of this invention having a promoting activity on the production of apolipoprotein E are useful as the therapeutic agents for neurologic damages, especially as an antidementia agent, and also as a therapeutic agent for hyperlipemia.

The depsipeptides of the invention or pharmacologically acceptable salts thereof may be prepared according to any methods conventionally employed for peptide synthesis. For example, there may be employed a condensing agent method, an azide method, a chloride method, an acid anhydride method, an active ester method, a redox method, an enzyme method or the like as disclosed in Nobuo Izumiya et al., "Fundamentals and Experiments for Peptide Synthesis (in Japanese)", issued from Maruzen Co., Ltd., 1985.

The depsipeptides presented by the formula (1) or pharmacologically acceptable salts thereof may be prepared, for example, by protecting or activating the carboxy group of a 3-hydroxypropionic acid derivative represented by the formula (5)

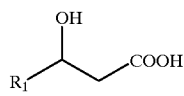

(5)

(wherein $R_1$ is as defined above) and condensing the product thus obtained successively with the desired amino acids according to a conventional method.

The protection of the carboxyl group in the compound of the formula (5) as depicted above may be carried out according to the esterification reaction for methyl esters by reacting with diazomethane in a solvent of ether, methanol or the like under ice-cooling or at room temperature or the esterification reaction for benzyl esters by reacting with benzyl bromide in the presence of a basic substance such as triethylamine in a solvent such as dimethylformamide (hereinafter referred to as "DMF"), dimethyl sulfoxide (hereinafter referred to as "DMSO") or the like at a temperature of from room temperature to heating temperature.

The condensation of an amino acid to the hydroxy group in a compound having the protected carboxyl group may be carried out by employing as a condensing reagent N,N'-dicyclohexylcarbodiimide (hereinafter referred to as "DCC") or 1-ethyl-3-(3'-dimethylaminopropyl) carbodiimide hydrochloride, i.e. water-soluble carbodiimide (hereinafter referred to as "WSCI") or the like in a solvent such as ether, chloroform, dichloromethane, ethyl acetate, DMF, tetrahydrofuran (hereinafter referred to as "THF"), acetonitrile, DMSO or the like under ice-cooling or at room temperature, preferably in the presence of an acylation catalyst such as dimethylaminopyridine (hereinafter referred to as "DMAP") or the like.

As the 3-hydroxycarboxylic acid of the formula (5) which is a starting material to be used for the depsipeptide of this invention, there may be illustratively mentioned 3-hydroxy-caprylic acid, 3-hydroxy-pelargonic acid, 3-hydroxy-capric acid, 3-hydroxy-lauric acid, 3-hydroxy-myristic acid, 3-hydroxy-palmitic acid, 3-hydroxy-margaric acid and 3-hydroxy-stearic acid.

In preparing the depsipeptide of the invention, when a condensing agent is to be used, there may be used DCC, WSCI, O-(1H-benzotriazol-1-yl)-N,N,N', N'-tetramethyluronium tetrafluoroborate (TBTU) or O-(7-azabenzotriazol-1-yl)-1,2,3-tetramethyluronium hexafluorophosphate (HATU) and the like. It is also preferable to simultaneously add an additive commonly employed for preventing racemization such as N-hydroxy-succinimide, N-hydroxybenzotriazole (hereinafter referred to as "HOBt"), N-hydroxy-5-norbornene-2,3-dicarbodiimide, 1-hydroxy-7-azabenzotriazole (HOAt) and the like.

When the azide method is applied, there may be employed preferably diphenylphosphoric acid azide (hereinafter referred to as "DPPA") and the like.

It is preferable to apply to the carboxyl group, amino group, (ω-carbamido group and the like any protecting procedure which would not participate in the said condensation reaction, according to any conventional and well-known procedures before carrying out the condensation reaction.

In this case various protecting groups as depicted above may be applied for the said protecting procedure.

The depsipeptides of the invention has the feature that at least one of A, B, D, E, F, G, J and Z is a N-substituted glycine, and a N-substituted glycine is to be used in place of one of the amino acids during the step of condensation of the amino acid. In this case, the N-substituted glycine is used for the condensation reaction after the amino group at the α-position or the carboxyl group is protected, and the protecting group for this case may be any of various protecting groups as depicted above.

Removal of the protecting group in the steps is required to leave the protecting group without giving any influence upon the peptide linkage and may be appropriately selected in compliance with the type of the protecting group used.

As the solvent which may be employed for each peptide synthesis as described above, there may be mentioned, for example, anhydrous or hydrous chloroform, dichloromethane, ethyl acetate, DMF, DMSO, pyridine, dioxane, THF, dimethoxyethane, acetonitrile, etc. and any combination of two or more thereof may be used if necessary. Also, this condensation reaction is carried out at a temperature ranging about −20 to 50° C. similarly to conventional condensation reactions.

For the present synthesis, there may be used any of a liquid phase method and a solid phase method, while a column method or a batch method may be also applicable herein.

The depsipeptide represented by the above formula (2) may be prepared according to a conventional peptide synthesis procedure as described below.

For example, the cyclic depsipeptide represented by the above formula (2) may be prepared by sequential steps of:
condensing the hydroxy group of a 3-hydroxy-propionic acid derivative represented by the formula (5)

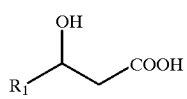

(5)

(wherein $R_1$ is as defined above) successively with necessary amino acid residues to form a depsipeptide represented by the formula (6)

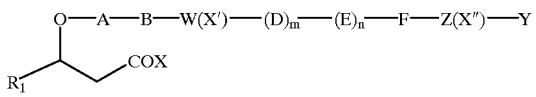
(6)

(wherein X is a protective group for the carboxy group, X' and X" are protective groups for the carboxy group of aspartic acid at the β-position thereof or the carboxy group of the glutamic acid at the γ-position thereof, the carbamino group of asparagine at the β-position thereof or the carbamido group of glutamine at the γ-position thereof, and A, B, W, D, E, F, Z, Y, $R_1$, m and n are as defined above), deprotecting the amino-protecting group in aspartic acid, asparagine, glutamic acid or glutamine in the depsipeptide thus obtained to form a depsipeptide represented by the formula (7)

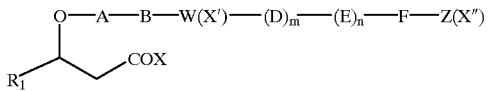
(6)

(wherein A, B, W, D, E, F, Z, X, X', X", $R_1$, m and n are as defined above), deprotecting the protecting group X for the carboxyl group in the depsipeptide thus obtained followed by self-condensation to form a cyclic depsipeptide represented by the formula (8)

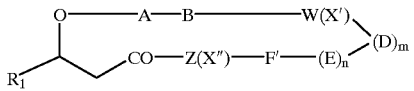
(8)

(wherein A, B, W, D, E, F, Z, X, X', X", $R_1$, m and n are as defined above), and deprotecting the carboxy group of aspartic acid at the β-position thereof, the carboxy group of glutamic acid at the γ-position thereof, the carbamido group of asparagine at the β-position thereof or the carbamido group of glutamine at the γ-position thereof in the cyclic depsipeptide thus obtained to form the depsipeptide represented by the above formula (2).

The depsipeptides represented by the above formula (1) or (2) may be prepared by stepwise condensations of amino acids one by one according to a conventional method for peptide synthesis and subsequent self-condensation or alternatively by condensation of some oligopeptides previously synthesized followed by self condensation.

The introduction of the N-substituted glycine residue of the formula (3) into the peptide chain in the depsipeptide of the present invention may be carried out by acylating the N-terminal amino group of the peptide with a halogenated acetic acid such as bromoacetic acid, and then reacting the resulting product with an amine of the formula (9)

$$H_2N—R_4—R_5 \quad (9)$$

(wherein $R_4$ and $R_5$ are as defined above).

The depsipeptides of the invention in the form of salts thereof may be converted to the corresponding free form, and the so-obtained depsipeptides of the invention in the form of the free form thereof may be converted to the corresponding pharmacologically acceptable salts thereof. In the latter case, when the depsipeptide is in the form of an acidic compound because of the carboxy group involved therein, there may be formed salts with inorganic bases such as sodium, potassium, calcium and ammonium salts or the like and with organic bases such as triethylamine salt, and when the depsipeptide is in the form of a basic compound because of the amino group involved therein, there may be formed salts with inorganic acids such as hydrochloric acid, hydrobromic acid, sulfuric acid and phosphoric acid or the like and with organic acids such as acetic acid, succinic acid, oxalic acid, tartaric acid or the like.

The depsipeptides or pharmacologically acceptable salts thereof according to this invention may be formulated to pharmaceutical preparations of various dosage forms. More specifically, such pharmaceutical preparations may be, for example, solid preparations such as tablets, hard capsules, soft capsules, granules, powders, etc. and liquid preparations such as solutions, emulsions, suspensions, etc. As the preparations for parenteral administration may be mentioned injections, suppositories, etc.

In preparing such pharmaceutical compositions, conventional additives may be incorporated, for example, excipients, stabilizers, antiseptics, solubilizing agents, wetting agents, emulsifying agents, lubricants, sweetening agents, coloring agents, flavoring agents, isotonic agents, buffering agents, antioxidants and the like.

As the additives, there may be mentioned, for example, starch, sucrose, fructose, lactose, glucose, mannitol, sorbitol, precipitated calcium carbonate, crystalline cellulose, carboxymethylcellulose, dextrin, gelatin, acacia, magnesium stearate, talc, hydroxypropyl-methylcellulose and the like.

Where the depsipeptide of the invention is to be applied in the form of solutions or injections, the depsipeptide of this invention may be used by dissolving or suspending in any conventional diluent. The diluent may include, for example, physiological saline, Ringer's solution, an aqueous glucose solution, an alcohol, a fatty acid ester, glycerol, a glycol, an oil derived from plant or animal sources, a paraffin and the like.

These preparations may be prepared according to a conventional method.

A usual clinical dose may be in the range of 1–2000 mg per day for adult when orally given. More preferably, it is in the range of 5–1000 mg.

The production of the depsipeptide of the invention will be illustrated below by way of Synthesis Examples, and the productivity of apolipoprotein E by the depsipeptide of this invention will be explained by way of Test Examples and Preparation Examples.

The following Referential Examples and Synthesis Examples illustrate but do not limit the production of the depsipeptides of the present invention.

The reactions in preparing Compounds (1) and (2) will be illustrated by way of the following Reaction Schemes 1–3:

Reaction Scheme 1
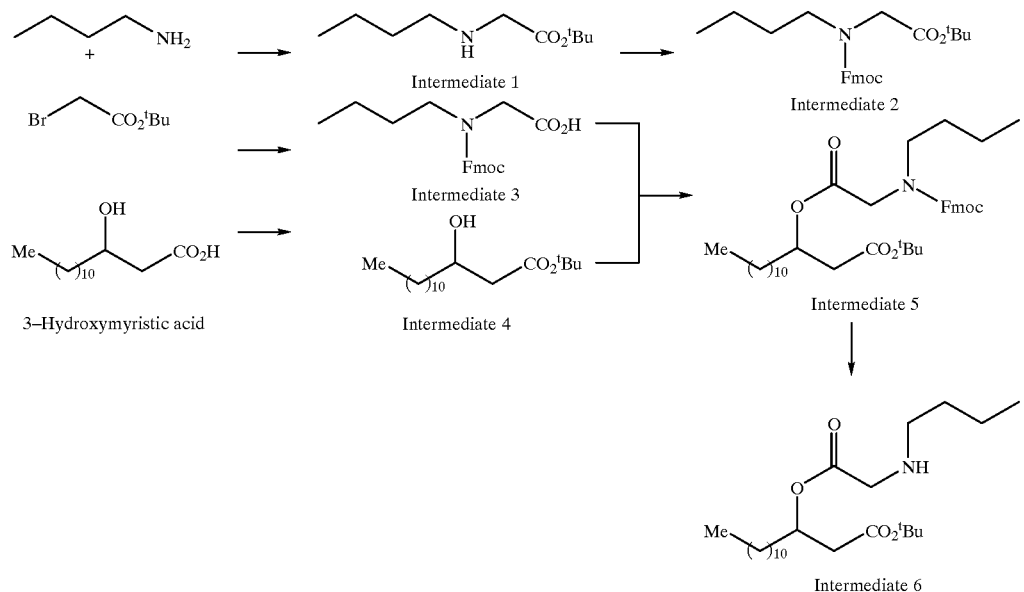
Reaction Scheme 2
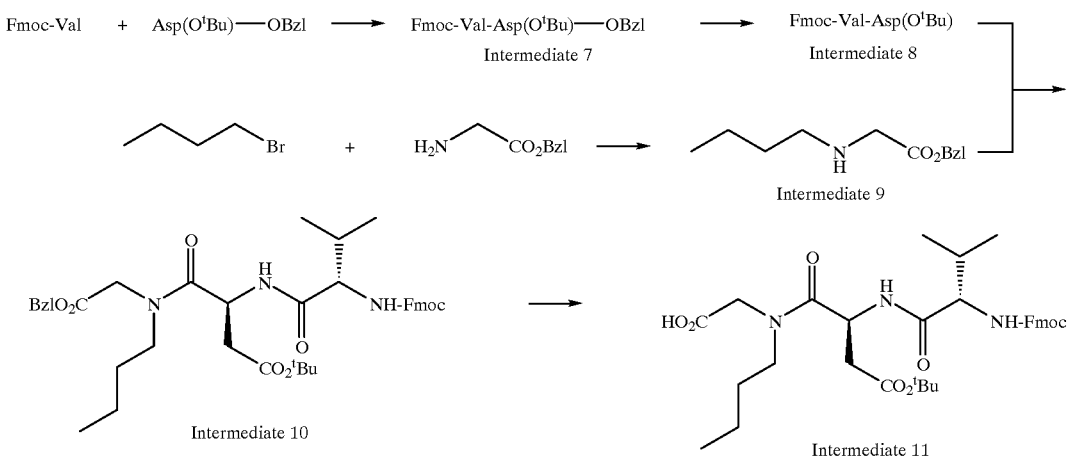

Reaction Scheme 3

Intermediate 6
+
Intermediate 11

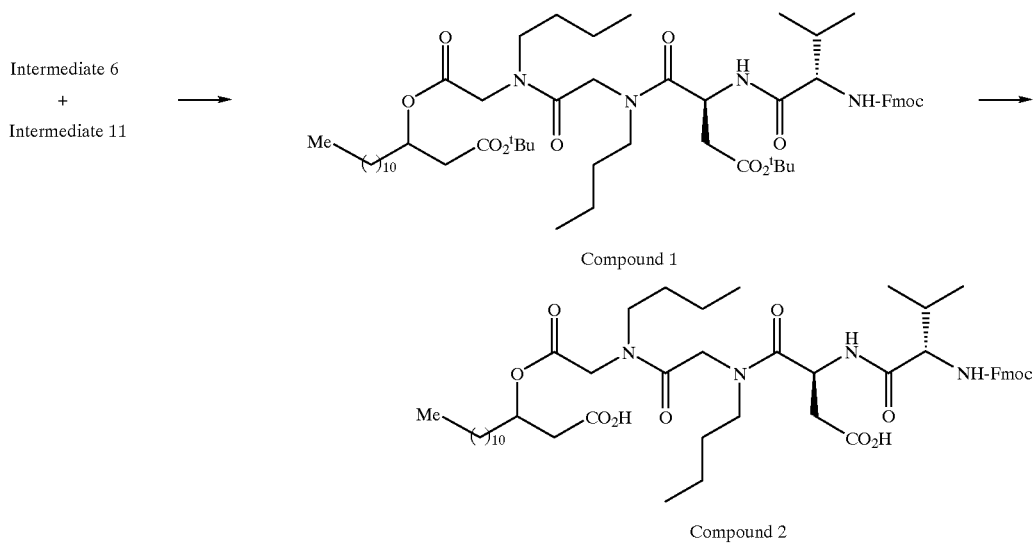

Compound 1

Compound 2

REFERENTIAL EXAMPLE 1
Preparation of Intermediate 1

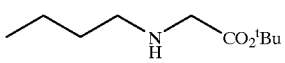

Intermediate 1

To a solution of n-butylamine (2.19 g) and triethylamine (4.2 ml) in toluene (30 ml) was added dropwise a solution of t-butyl bromoacetate (5.66 g) in toluene (10 ml). Then, the reaction solution was stirred at room temperature for 2 days. After the crystalline substance separated out was filtered, the solvent was removed in vacuo. The crude product thus obtained was purified by a silica gel column chromatography to afford 4.56 g of Intermediate 1.

$^1$H-NMR (CDCl$_3$, 400 MHz) δ 3.29 (s, 2H), 2.58 (t, J=7.1 Hz, 2H), 1.61 (br s, 1H), 1.47 (s, 9H), 1.31–1.51 (m, 4H), 0.92 (t, J=7.3 Hz, 3H)

REFERENTIAL EXAMPLE 2
Preparation of Intermediate 2

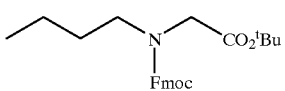

Intermediate 2

To an aqueous solution (50 ml) of sodium carbonate (5.10 g) was added a DMF solution (50 ml) of Intermediate 1 (4.6 g) and then a DMF solution (50 ml) of N-Fmoc-succinimide (9.86 g) was added with stirring under ice-cooling. The resulting mixture was stirred for 30 minutes. To the reaction solution was added water and extracted with ethyl acetate. The organic layer was dried over anhydrous sodium sulfate, the solvent was removed in vacuo and the residue was purified by a silica gel column to afford Intermediate 2 (7.90 g).

$^1$H-NMR (CDCl$_3$, 400 MHz) δ 7.75 (d, J=7.3 Hz, 2H), 7.60–7.58 (m, 2H), 7.41–7.37 (m, 2H), 7.33–7.28 (m, 2H), 4.49 (d, J=6.3 Hz, 1H), 4.36 (d, J=6.8 Hz, 1H), 4.27–4.20 (m, 1H), 3.88 and 3.87 (s, 2H), 3.35 and 3.17 (m, 2H), 1.46 and 1.45 (s, 9H), 1.56–1.13 (m, 4H), 0.93 and 0.86 (t, J=7.3 Hz, 3H)

REFERENTIAL EXAMPLE 3
Preparation of Intermediate 3

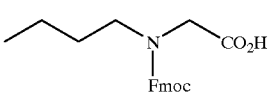

Intermediate 3

To a solution of Intermediate 2 (7.87 g) in dichloromethane (5 ml) was added TFA (11 ml) and the resulting mixture was stirred at room temperature for 5 hours. The reaction solution was concentrated under reduced pressure, the residue was diluted with dichloromethane (100 ml) and washed with water. The organic layer was dried over anhydrous sodium sulfate and concentrated under reduced pressure to afford Intermediate 3 (6.91 g). The product was used for the subsequent reaction without any purification.

$^1$H-NMR (CDCl$_3$, 400 MHz) δ 9.87 (br, 1H), 7.77–7.71 (m, 2H), 7.59–7.52 (m, 2H), 7.41–7.25 (m, 4H), 4.54–4.45 (m, 2H), 4.27–4.11 (m, 1H), 4.00 and 3.87 (s, 2H), 3.33–3.29 and 3.17–3.14 (m, 2H), 1.51–1.10 (m, 4H), 0.91 and 0.85 (t, J=7.3 Hz, 3H)

REFERENTIAL EXAMPLE 4
Preparation of Intermediate 4

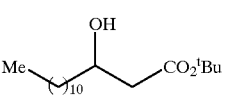

Intermediate 4

To a suspension of 3-hydroxymyristic acid (10.3 g) in t-butyl acetate (250 ml) was added boron trifluoride ethyl etherate (20 ml) while stirring in an ice bath, and the mixture was stirred under ice-cooling for one hour. The reaction solution was poured into water and the organic layer was separated. The aqueous layer was adjusted to a pH value of about 5 by the addition of aqueous saturated potassium carbonate and then extracted with ethyl acetate. The extract was combined with the organic layer thus separated and dried over anhydrous sodium sulfate. The solvent was removed in vacuo and the residue was purified by a silica gel column chromatography to afford Intermediate 4 (7.96 g).

$^1$H-NMR (CDCl$_3$, 400 MHz) δ 3.97–3.94 (m, 1H), 3.06 (d, J=3.7 Hz, 1H), 2.42 (dd, J=2.9, 16 Hz, 1H), 2.31 (dd, J=9.0, 16 Hz, 1H), 1.47 (s, 9H), 1.30–1.19 (m, 2H), 0.88 (t, J=6.8 Hz, 3H)

REFERENTIAL EXAMPLE 5
Preparation of Intermediate 5

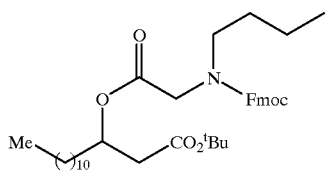

Intermediate 5

To a solution of Intermediate 3 (2.65 g) in dichloromethane (15 ml) were added successively Intermediate 4 (1.50 g) and 4-dimethylaminopyridine (0.12 g). After cooling, DCC (1.70 g) was added to the reaction solution and the resulting mixture was stirred under ice-cooling for 20 minutes and then at room temperature for 2.5 hours. After insolubles were removed by filtration, the solvent was he removed in vacuo from the filtrate and the residue was purified by a silica gel column chromatography to afford Intermediate 5 (2.75 g).

$^1$H-NMR (CDCl$_3$, 400 MHz) δ 7.77–7.74 (m, 2H), 7.60–7.51 (m, 2H), 7.41–7.37 (m, 2H), 7.33–7.28 (m, 2H), 5.28–5.20 (m, 1H), 4.51–3.86 (m, 5H), 3.37–3.33 and 3.20–3.15 (m, 2H), 2.54–2.40 (m, 2H), 1.56–1.15 (m, 33H), 0.89–0.84 (m, 3H)

REFERENTIAL EXAMPLE 6
Preparation of Intermediate 6

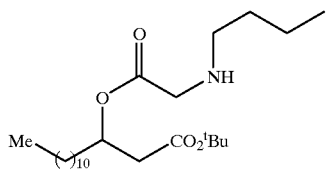

Intermediate 6

To a solution of Intermediate 5 (0.63 g) in DMF (4 ml) was added diethylamine (0.4 ml) and the mixture was stirred for one hour. The reaction solution was concentrated under reduced pressure and the residue was purified by a silica gel column chromatography to afford Intermediate 6 (0.37 g).

$^1$H-NMR (CDCl$_3$, 400 MHz) δ 5.30–5.23 (m, 1H), 3.39 (d, J=17 Hz, 1H), 3.34 (d, J=17 Hz, 1H), 2.59 (t, J=7.3 Hz, 2H), 2.52–2.43 (m, 2H), 1.51–1.25 (m, 33H), 0.93–0.86 (m, 6H)

REFERENTIAL EXAMPLE 7
Preparation of Intermediate 7
Fmoc-Val-Asp(O$^t$Bu)-OBzl Intermediate 7

To a solution of L-aspartic acid α-benzyl-β-tert-butyl ester (2.50 g) in dichloromethane (100 ml) were added successively Fmoc-L-valine (3.39 g) and HOBt monohydrate (1.68 g). The reaction solution was cooled with ice, WSCI (2.49 g) was added and the mixture was stirred under ice-cooling for 20 minutes and then at room temperature for 11 hours. The reaction solution was washed successively with aqueous sodium hydrogencarbonate and saturated aqueous sodium chloride and then dried over anhydrous sodium sulfate. The solvent was removed in vacuo and the residue was purified by a silica gel column chromatography to afford Intermediate 7 (3.24 g).

$^1$H-NMR (CDCl$_3$, 400 MHz) δ 7.76 (d, J=7.8 Hz, 2H), 7.59 (d, J=7.3 Hz, 2H), 7.41–7.27 (m, 9H), 6.77 (d, J=8.3 Hz, 1H), 5.42 (d, J=8.8 Hz, 1H), 5.22–5.19 (m, 1H), 4.43–4.04 (m, 4H), 3.00 (dd, J=3.9, 17 Hz, 1H), 2.70 (dd, J=3.9, 17 Hz, 1H), 2.12–2.10 (m, 1H), 1.39 (s, 9H), 0.96 (d, J=6.3 Hz, 3H), 0.91 (d, J=6.3 Hz, 3H)

REFERENTIAL EXAMPLE 8

Preparation of Intermediate 8

Fmoc-Val-Asp(OtBu) Intermediate 8

In a solution of Intermediate 7 (3.23 g) in methanol (200 ml) was suspended 10% palladium-carbon (0.56 g) and the resulting suspension was stirred at room temperature under hydrogen atmosphere (one atmospheric pressure) for one hour. The catalyst was removed by filtration and the solvent was removed in vacuo from the filtrate. To the residue was added diisopropyl ether. The crystalline substance thus separated out was recovered by filtration and dried under reduced pressure to afford Intermediate 8 (1.68 g).

$^1$H-NMR (CDCl$_3$, 400 MHz) δ 8.12 (d, J=8.3 Hz, 1H), 7.86 (d, J=7.8 Hz, 2H), 7.74–7.70 (m, 2H), 7.42–7.38 (m, 2H), 7.34–7.30 (m, 5H), 4.59–4.53 (m, 1H), 4.29–4.21 (m, 3H), 3.91–3.87 (m, 1H), 2.71–2.52 (m, 2H), 1.99–1.95 (m, 1H), 1.36 (s, 9H), 0.89–0.85 (m, 6H)

REFERENTIAL EXAMPLE 9

Preparation of Intermediate 9

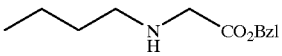

Intermediate 9

To a solution of glycine benzyl ester p-toluenesulfonate (5.00 g) in DMF (10 ml) were added successively triethylamine (5.2 ml) and n-butyl bromide (1.6 ml) while stirring at room temperature. The resulting mixture was stirred at room temperature for 2 hours and then at 60° C. for 1.5 hours. The reaction solution was poured into water and extracted with ethyl acetate. The organic layer was washed with saturated aqueous sodium chloride and dried over anhydrous sodium sulfate and then the solvent was removed in vacuo. The residue was purified by a silica gel column chromatography to afford Intermediate 9 (1.83 g).

$^1$H-NMR (CDCl$_3$, 400 MHz) δ 7.36–7.32 (m, 5H), 5.17 (s, 2H), 3.45 (s, 2H), 2.60 (t, J=6.8 Hz, 2H), 1.60 (bs, 1H), 1.51–1.43 (m, 2H), 1.40–1.31 (m, 2H), 0.91 (t, J=7.3 Hz, 3H)

REFERENTIAL EXAMPLE 10

Preparation of Intermediate 10

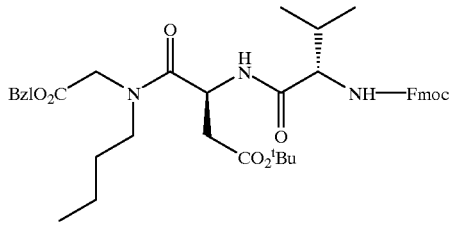

Intermediate 10

To a solution of Intermediate 8 (0.51 g) in dichloromethane (5 ml) were added successively HOAt (0.15 g) and diisopropylethylamine (0.35 ml) while stirring at room temperature. The reaction solution was cooled with ice and HATU (1.25 g) and a solution of Intermediate 9 (0.44 g) in dichloromethane (2 ml) were added successively. The resulting mixture was stirred under ice-cooling for 5 minutes and then at room temperature for 12 hours. The reaction solution was washed with 0.5N hydrochloric acid and dried over anhydrous sodium sulfate and then the solvent was removed in vacuo. The residue was purified by a silica gel column chromatography to afford Intermediate 10 (0.58 g).

$^1$H-NMR (CDCl$_3$, 400 MHz) δ 7.76 (d, J=7.3 Hz, 2H), 7.59 (d, J=6.8 Hz, 2H), 7.41–7.30 (m, 9H), 5.36–5.11 (m, 4H), 4.46–4.00 (m, 7H), 3.43–3.35 (m, 2H), 2.74–2.46 (m, 2H), 2.13–2.09 (m, 1H), 1.59–1.24 (m, 13H), 0.94–0.83 (m, 9H)

REFERENTIAL EXAMPLE 11

Preparation of Intermediate 11

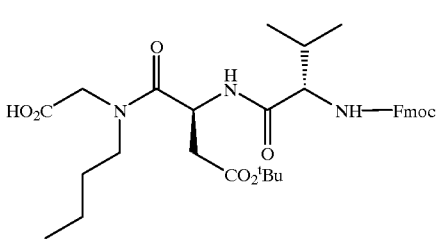

Intermediate 11

In a solution of Intermediate 10 (0.53 g) in methanol (50 ml) was suspended 10% palladium-carbon (0.18 g) and the resulting suspension was stirred under hydrogen atmosphere (one atmospheric pressure) at room temperature for one hour. The catalyst was removed by filtration and the solvent was removed in vacuo from the filtrate to afford Intermediate 11 (0.45 g). This product was used for the subsequent reaction without any purification.

Synthesis Example 1

Preparation of Compound 1

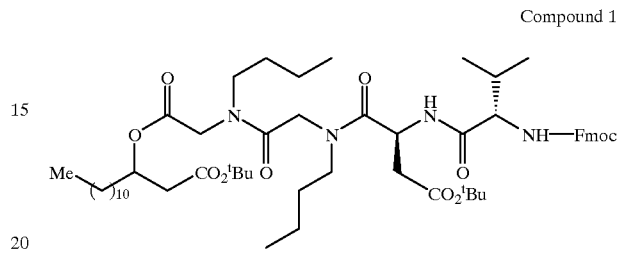

Compound 1

To a solution of Intermediate 11 (0.38 g) in dichloromethane (10 ml) were added successively HOAt (91 mg) and diisopropylethylamine (0.2 ml) while stirring at room temperature. The reaction solution was cooled with ice and HATU (0.28 g) and a solution of Intermediate 6 (0.35 g) in dichloromethane (5 ml) were added successively. The resulting mixture was stirred under ice-cooling for 5 minutes and then at room temperature for 11 hours. The reaction solution was washed successively with 0.25N hydrochloric acid and saturated aqueous sodium chloride and dried over anhydrous sodium sulfate and then the solvent was removed in vacuo. The residue was purified by a silica gel column chromatography to afford Compound 1 (0.44 g).

Mass spectrum (ESI) m/z 1019.6 (MH+)

Synthesis Example 2

Preparation of Compound 2

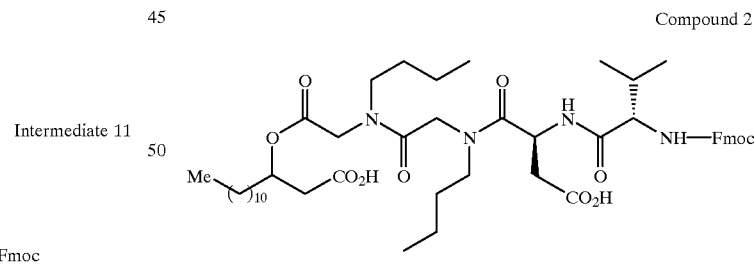

Compound 2

A mixture of Compound 1 (0.44 g) and trifluoroacetic acid (4 ml) was stirred at room temperature for 2.5 hours. The reaction solution was diluted with chloroform (10 ml) and washed with water (10 ml×3). The organic layer was dried over anhydrous sodium sulfate and the solvent was removed in vacuo to afford Compound 2 (0.35 g).

Mass spectrum (ESI) m/z 907.5 (MH+)

The Synthesis of Compounds 3–6 will be shown in Referential Example 12 and Synthesis Examples 3–6.

REFERENTIAL EXAMPLE 12

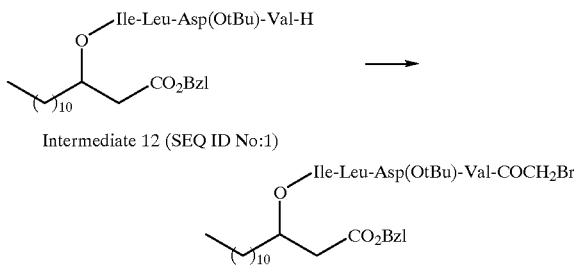

Intermediate 12 (SEQ ID No:1)

To a solution of benzyl 3-(L-valyl-L-(tert-butyl) -α-aspartyl-L-leucyl-L-isoleucyl)oxytetradecanoate (1.91 g), bromoacetate (0.35 g) and HOBt monohydrate (0.39 g) in dichloromethane (20 ml) was added WSCI (0.48 g) under ice-cooling. The mixture was stirred under ice-cooling for one hour and then at room temperature overnight. The solvent was removed in vacuo and ethyl acetate and a 10% aqueous citric acid solution were added. The organic layer obtained by separation was washed successively with water, a 5% aqueous sodium hydrogencarbonate solution, water and a saturated sodium chloride solution and dried over anhydrous sodium sulfate. After the solvent was removed in vacuo, the crude product was purified by silica gel column chromatography to give 1.05 g of Intermediate 12.

$^1$H-NMR (CDCl$_3$, 400 MHz): 7.24–7.41 (m, 6H), 7.09 (d, J=7.8 Hz, 1H), 6.98 (d, J=7.8 Hz, 1H), 6.56 (t, J=8.5 Hz, 1H), 5.22–5.32 (m, 1H), 5.12 (d, J=12 Hz, 1H), 5.08 (d, J=12 Hz, 1H), 4.67–4.75 (m, 1H), 4.46–4.53 (m, 1H), 4.36–4.45 (m, 1H), 4.24 (t, J=6.8 Hz, 1H), 4.10 (s, 2H), 2.93 (dd, J=3.9, 17 Hz, 1H), 2.55–2.72 (m, 3H), 2.16–2.27 (m, 1H), 1.79–1.97 (m, 1H), 1.52–1.75 (m, 5H), 1.44 (s, 9H), 1.05–1.48 (m, 20H), 1.00 (d, J=6.8 Hz, 3H), 0.98 (d, J=6.8 Hz, 3H), 0.80–0.96 (m, 15H).

Synthesis Example 3
Preparation of Compound 3

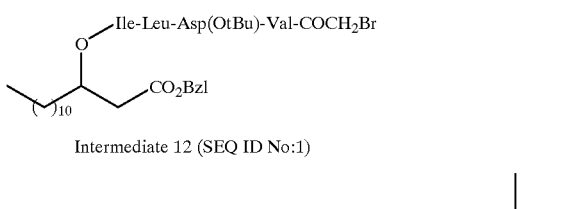

Intermediate 12 (SEQ ID No:1)

Compound 3 (SEQ ID No: 2)

A solution of Intermediate 12 (1.40 g) and isobutylamine (0.29 ml) in DMSO (10 ml) was stirred at room temperature for 2 hours. After diluted with ethyl acetate, the reaction mixture was washed successively with a 5% aqueous sodium hydrogencarbonate solution, water and a saturated sodium chloride solution and dried over anhydrous sulfate. The solvent was removed in vacuo and WSCI (0.36 g) was added to a solution of the resulting crude product (1.41 g), Fmoc-Leu-OH (0.69 g) and HOBt monohydrate (20 ml) in DMF (20 ml) under ice-cooling. The resulting reaction mixture was stirred under ice-cooling for 2 hours and then at room temperature overnight. After the solvent was removed in vacuo, ethyl acetate and a 10% aqueous citric acid solution were added to the resulting residue. The organic layer obtained by separation was washed successively with water, a 5% aqueous sodium hydrogencarbonate solution, water and a saturated sodium chloride solution and dried over anhydrous sodium sulfate. After the solvent was removed in vacuo, the resulting crude product was purified by silica gel column chromatography to afford 1.67 g of Compound 3.

$^1$H-NMR (CDCl$_3$, 400 MHz) 7.75 (d, J=7.3 Hz, 2H), 7.55–7.63 (m, 2H), 7.21–7.44 (m, 10H), 7.05–7.11 (m, 1H), 6.73 (t, J=7.3 Hz, 1H), 6.57 (d, J=4.9 Hz, 1H), 5.98 (d, J=9.3 Hz, 1H), 5.26 (br s, 1H), 5.06–5.13 (m, 2H), 4.66–4.80 (m, 2H), 4.36–4.52 (m, 3H), 4.05–4.33 (m, 2H), 3.80 (d, J=16 Hz, 1H), 3.37 (dd, J=7.3, 15 Hz, 1H), 3.27 (dd, J=8.5, 15 Hz, 1H), 2.86–2.98 (m, 1H), 2.65–2.80 (m, 2H), 2.52–2.61 (m, 1H), 2.03–2.25 (m, 2H), 1.51–1.94 (m, 11H), 1.43 (s, 9H), 1.06–1.48 (m, 20H), 0.69–1.05 (m, 33H).

Synthesis Example 4
Preparation of Compound 4

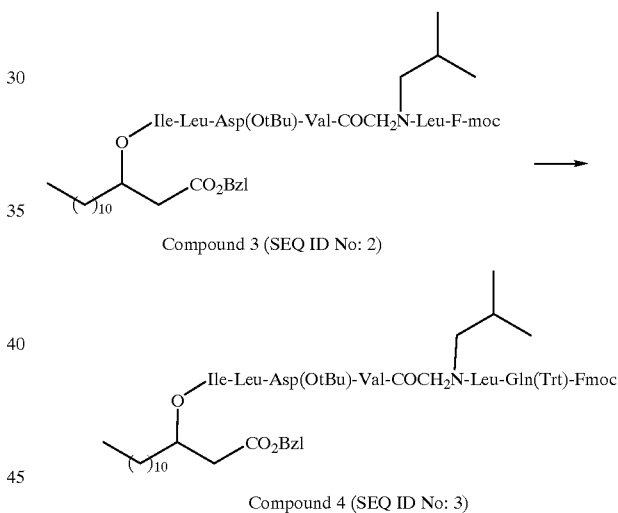

Compound 3 (SEQ ID No: 2)

Compound 4 (SEQ ID No: 3)

To a solution of Compound 3 (1.67 g) in DMF (13 ml) was added diethylamine (1.3 ml) and the solution was stirred at room temperature for 30 minutes. After the solvent was removed in vacuo, the resulting crude product was purified by silica gel column chromatography to give a deprotected amine compound (1.12 g). WSCI (0.25 g) was added to a solution of the deprotected amine compound (1.12 g), Fmoc-Gln(Trt) (0.79 g), HOBt monohydrate (0.20 g) in DMF (10 ml) under ice-cooling. The reaction mixture was stirred under ice-cooling for 2 hours and then at room temperature overnight. After the solvent was removed in vacuo, ethyl acetate and a 10% aqueous citric acid solution were added to the residue. The organic layer obtained by separation was washed successively with water, a 5% sodium hydrogencarbonate solution, water and a saturated sodium chloride solution and dried over anhydrous sodium sulfate. After the solvent was removed in vacuo, the resulting crude product was purified by silica gel column chromatography to give 1.69 g of Compound 4.

Mass spectrum (ESI) m/z 1649 (M+1)$^+$

Synthesis Example 5

Preparation of Compound 5

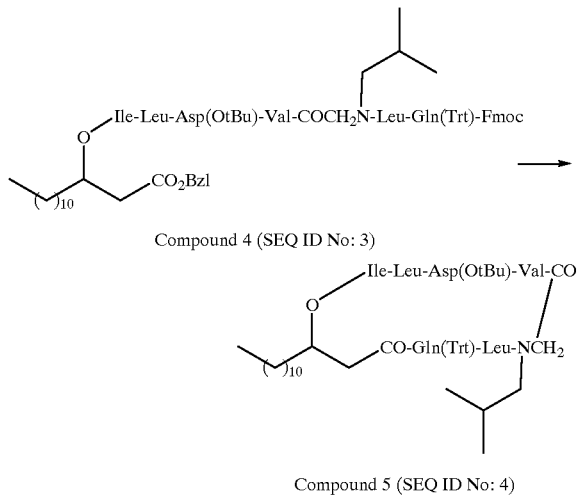

Compound 4 (SEQ ID No: 3)

Compound 5 (SEQ ID No: 4)

A suspension of Compound 4 (1.69 g) and 10% Pd—C (1.6 g) in methanol (50 ml) was subjected to reaction under hydrogen atmosphere at room temperature for 4 hours. After completion of the reaction, the 10% Pd—C was filtrated off and the solvent was removed in vacuo form the filtrate. The residue was dissolved in a 20% piperidine solution in DMF (35 ml) and the solution was stirred at room temperature for 1.5 hours. The solvent was removed in vacuo to give a crude product. To a solution of the crude product in DMF (1.3 l) were added diisopropylethylamine (0.67 ml), HOAt (0.39 g) and HATU (1.09 g), followed by stirring at room temperature for 2 days. After the solvent was removed in vacuo, ethyl acetate and a 5% aqueous potassium hydrogen sulfate solution were added to the resulting residue. The organic layer was separated, washed with water and a saturated aqueous sodium chloride solution and dried over anhydrous sodium sulfate. After the solvent was removed in vacuo, the resulting crude product was purified by silica gel column chromatography to afford Compound 5 (0.76 g).

Mass spectrum (ESI) m/z 1319 (M+1)$^+$

Synthesis Example 6

Preparation of Compound 6

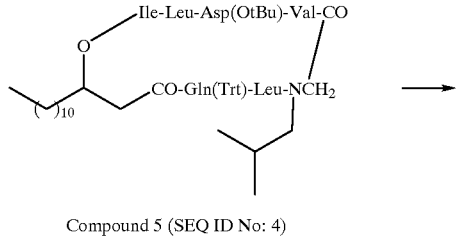

Compound 5 (SEQ ID No: 4)

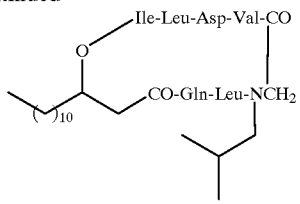

Compound 6 (SEQ ID No: 5)

A solution of Compound 5 (0.76 g) in trifluoroacetate (10 ml) was stirred at room temperature for one hour. After the solvent was removed in vacuo, the resulting crude product was purified by silica gel column chromatography to obtain 0.48 g of Compound 6.

Mass spectrum (ESI) m/z 1021 (M+1)$^+$

Test Example

It will be shown below that the depsipeptides of the invention may influence upon the productivity of apolipoprotein E in Hep G2 cells, together with the test procedure as used.

First, Hep G2 cells of 1×10$^5$ cells were suspended in Dulbecco's modified Eagle medium (manufactured by Nissui Seiyaku Co., Ltd.; hereinafter referred to as "D-MEM medium") containing 10% fetal bovine serum and 1 ml each of the suspension was poured into a 24-well tissue culture plate. The cells were cultivated at 37° C. under atmosphere of a mixed gas composed of 5% carbon dioxide and 95% air. After 3 days, the medium was removed by means of a pipette, 1 ml of a fresh D-MEM medium was added and then 10 μl of a methanolic solution of the depsipeptide of the invention was further added at the concentration as shown in Table 1. After 18 hours, the medium was again replaced with D-MEM medium, 10 μl of a methanolic solution of the depsipeptide was added and cultivation was further conducted at 37° C. for 8 hours. The supernatant thus obtained was used as a sample solution. The apolipoprotein E produced in the cultured broth was assayed by means of an enzyme immunoassay method.

The compositions of the buffers applied in the enzyme immunoassay are summarized below. PBS represents phosphate-buffered saline, PBS-T represents phosphate-buffered saline having incorporated Tween 20 and a blocking solution is the phosphate buffer containing the immunosuppressive agent "Block Ace" which is derived from lactoprotein and manufactured by Dainippon Pharmaceutical Co., Ltd.

| PBS (pH 7.2) | |
|---|---|
| KH$_2$PO$_4$ | 0.2 g |
| Na$_2$HPO$_4$.12H$_2$O | 2.9 g |
| NaCl | 8.0 g |
| KCl | 0.2 g |
| Distilled water | q.s. |
| Total | 1000 ml |
| PBS-T (pH 7.2) | |
| KH$_2$PO$_4$ | 0.2 g |
| Na$_2$HPO$_4$.12H$_2$O | 2.9 g |
| NaCl | 8.0 g |
| KCl | 0.2 g |
| Tween 20 | 0.5 g |

| -continued | |
| --- | --- |
| Distilled water | q.s. |
| Total | 1000 ml |
| Blocking solution (pH 7.2) | |
| Block Ace | 250 ml |
| $KH_2PO_4$ | 0.2 g |
| $Na_2HPO_4.12H_2O$ | 2.9 g |
| NaCl | 8.0 g |
| KCl | 0.2 g |
| Distilled water | q.s. |
| Total | 1000 ml |

1) Determination of apolipoprotein E

The mouse antihuman apolipoprotein E monoclonal antibody (manufactured by BYOSIS, S. A., France) was dissolved in a 0.05M aqueous sodium hydrogencarbonate solution (pH 9.5) at a concentration of 5 μg/ml. 50 μl each of the solution was poured into Nunc immunoplates which were then allowed to stand at 4° C. for 16 hours. They were washed three times with 300 μl of PBS, 300 μl of the blocking solution was added and the mixture was allowed to stand at 37° C. for 2 hours and then at 4° C. for 16 hours.

It was again washed three times with 300 μl of PBS, 50 μl of the above sample solution (the medium for Hep G2 cells) was added and the mixture was allowed to stand at room temperature for 2 hours. After washing three times with 300 μl of PBS-T, 50 μl of a 3000-fold diluted solution (10% aqueous Block Ace solution) of goat anti-apolipoprotein E polyclonal antibody (manufactured by Chemicon Co., Ltd., U.S.A.) was added and the mixture was allowed to stand at room temperature for 2 hours. The mixture was washed three times with 300 μl of PBS-T, a 5000-fold diluted solution (a 10% aqueous solution of Block Ace) of a peroxidase-labeled anti-goat TgG polyclonal antibody (manufactured by Bindingsite Co., Ltd., U. K.) was added and the mixture was allowed to stand at room temperature for 2 hours. After washing five times with 300 μl of PBS-T, 100 μl of a coloring solution (Composition: 0.1M potassium citrate (pH 4.5) 1 ml, 30% aqueous hydrogen peroxide 0.4 μl, orthophenylenediamine 1 mg) was added and the mixture was allowed to stand for 2 minutes. The reaction was quenched by the addition of 100 μl of 2N sulfuric acid and absorbance was measured at 490 nm using absorbance at 650 nm as a control. An amount of apolipoprotein E in the present depsipeptide was determined upon the calibration curve drawn up when a commercially available apolipoprotein E (Chemicon Co., Ltd., U.S.A.) was used as a standard.

In the Test Example, the same procedure as described above was carried out except that methanol alone was added instead of the methanolic solution of the depsipeptide of this invention and an apolipoprotein E amount was measured as a control. A relative apolipoprotein E amount by the present depsipeptide was represented in terms of a relative value (%) when the control was defined as 100.

As shown in Table 1, it was proved that the depsipeptides of the invention have a potent promoting activity on the productivity of apolipoprotein E at 1 or 5 μM.

TABLE 1

| Compound | Conc. (μM) | Relative amount of apolipoprotein E (%) |
| --- | --- | --- |
| 2 | 1 | 256 |
| 2 | 5 | 389 |

Preparation Examples

Examples for the pharmaceutical preparations containing as an active ingredient the depsipeptide of the invention will be given below.

Preparation Example 1

Tablets (per tablet)

| | |
| --- | --- |
| Compound 2 | 20 mg |
| Magnesium silicate | 20 mg |
| Lactose | 98.5 mg |
| Hydroxypropylcellulose | 7.5 mg |
| Magnesium stearate | 1 mg |
| Hydrogenated vegetable oil | 3 mg |
| Total | 150 mg |

Compound 2, magnesium silicate and lactose were admixed and kneaded with an alcoholic solution of hydroxypropylcellulose and then granulated to appropriate particle size, dried, and sized. Then, magnesium stearate and hydrogenated vegetable oil were added and blended to form uniform granules. The granules were then prepared to tablets, each having a diameter of 7.0 mm, a weight of 150 mg and a hardness of 6 kg, by means of a rotary tableting machine.

Preparation Example 2

Granules

| | |
| --- | --- |
| Compound 2 | 10 mg |
| Magnesium oxide | 40 mg |
| Dibasic calcium phosphate | 38 mg |
| Lactose | 10 mg |
| Hydroxypropylcellulose | 20 mg |

All materials of the above formulation except for hydroxypropylcellulose were uniformly admixed, kneaded with an alcoholic solution of hydroxypropylcellulose and then granulated by means of an extrusion granulation machine and dried to form granules. The granules were sized so as to pass through a 12 mesh sieve and remain on a 48 mesh sieve, whereby granules were prepared.

Preparation Example 3

Syrups

| | |
| --- | --- |
| Compound 2 | 1.000 g |
| Sucrose | 30.000 g |
| D-Sorbitol 70 w/v% | 25.000 g |
| Ethyl paraoxybenzoate | 0.030 g |
| Propyl paraoxybenzoate | 0.015 g |
| Flavoring agent | 0.200 g |
| Glycerol | 0.150 g |

| | |
|---|---|
| 96% Ethanol | 0.500 g |
| Purified water | q.s. |
| Total | 100 ml |

Sucrose, D-sorbitol, ethyl paraoxybenzoate, propyl paraoxybenzoate and Compound 2 were dissolved in purified water (warm water). After cooling, a solution of flavoring agent in glycerol and ethanol was added and then purified water was added to the mixture to make up a volume to 100 ml.

Preparation Example 4

Injections

| | |
|---|---|
| Sodium salt of Compound 2 | 10.0 mg |
| Sodium chloride | 81.0 mg |
| Sodium hydrogencarbonate | 8.40 mg |
| Distilled water for injection | q.s. |
| Total | 10.0 ml |

Sodium hydrogencarbonate, sodium chloride and sodium salt of Compound 2 were dissolved in distilled water to make up a total amount to 10.0 ml.

Preparation Example 5

Suppositories

| | |
|---|---|
| Compound 2 | 2 g |
| Macrogol 4000 | 20 g |
| Glycerol | 78 g |
| Total | 100 g |

Compound 2 was dissolved in glycerol and then Macrogol 4000 was added and dissolved by warming. Then, the mixture was injected into a suppository die and solidified by cooling to prepare suppositories, each weighing 1.5 g.

What is claimed is:

1. A depsipeptide having the formula (2):

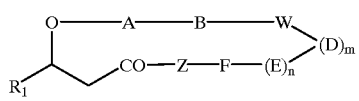

wherein $R_1$ is a straight or branched alkyl group of 5–20 carbon atoms or a straight or branched alkoxymethyl group of 5–15 carbon atoms;

A, B, D, E and F independently are a N-substituted glycine residue having the formula (3)

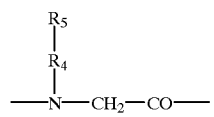

in which $R_4$ is an alkylene group of 1–4 carbon atoms and $R_5$ is a hydrogen atom, a hydroxy group, a carboxy group or a carbamido group; or A, B, D, E and F independently are a residue of an amino acid selected from the group consisting of alanine, valine, leucine, isoleucine, serine, threonine, lysine, hydroxylysine, arginine, cysteine, methionine, phenylalanine, tyrosine, tryptophan, histidine, proline, 4-hydroxyproline, piperidine-4-carboxylic acid, homoproline, octahydroindole-2-carboxylic acid, norvaline, norleucine, α-t-butylglycine, cyclohexylglycine, azetidine-2-carboxylic acid, 3-(3-pyridyl)alanine, (3-N-methyl)piperidylalanine, 3-(2-naphthyl)alanine, β-cyclohexylalanine, β-t-butylalanine, 9-anthracenylalanine, α-methylalanine, 2-aminobutanoic acid, aspartic acid, asparagine, glutamic acid and glutamine; wherein said residue of an amino acid is optionally substituted at the α-nitrogen atom with a ($C_1$–$C_4$) alkyl group;

W is a residue of an amino acid selected from the group consisting of aspartic acid, glutamic acid and an amino acid of the formula (4)

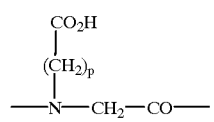

wherein p is an integer of 1–4;

Z is a residue of an amino acid selected from the group consisting of aspartic acid, asparagine, glutamic acid, glutamine, alanine, serine and lysine or the N-substituted glycine residue of the formula (3);

m and n are independently 0 or 1;

provided that a free amino group, a free carboxy group, a free hydroxy group, a free mercapto group or a free ω-carbamido group possibly existing in said amino acid residues for the above A, B, D, E, F, W and Z may be protected by a group used as a protecting group in peptide chemistry; and further provided that when A, B, D, E, F, W and Z are a residue of lysine, hydroxylysine, glutamic acid or aspartic acid, either α- or ω-amino or carboxyl group existing in said residue may form the peptide linkage with its adjacent amino acid; and further provided that at least one of A, B, D, E, F, W and Z is the N-substituted glycine residue of the formula (3);

or a pharmacologically acceptable salt thereof.

2. The depsipeptide of the formula (2) as claimed in claim 1 wherein A, B, D, E and F independently are the N-substituted glycine residue of the formula (3) or a residue of an amino acid selected from the group consisting of alanine, valine, leucine, isoleucine, phenylalanine, tyrosine, proline, β-t-butylalanine and aspartic acid; W is a residue of an amino acid selected from the group consisting of aspartic acid, glutamic acid and the amino acid of the formula (4); Z is a residue of an amino acid selected from the group consisting of aspartic acid, asparagine, glutamic acid, glutamine, alanine, serine and lysine or the N-substituted glycine residue of the formula (3), and at least one of A, B, D, E, F and Z is the N-substituted glycine residue of the formula (3); and m and n are 1, or a pharmacologically acceptable salt thereof.

3. The depsipeptide of the formula (2) as claimed in claim 1 wherein A is a N-($C_1$–$C_4$) alkylglycine residue of the formula (3); B is a residue of an amino acid selected from the group consisting of leucine, isoleucine, phenylalanine, β-t-butylalanine and aspartic acid; D is a residue of an amino acid selected from the group consisting of valine, phenylalanine, alanine and aspartic acid; E and F are each independently residues of an amino acid selected from the group consisting of leucine, isoleucine and alanine; W is a residue of an amino acid selected from the group consisting of aspartic acid, glutamic acid and the amino acid of the formula (4); Z is a residue of an amino acid selected from the group consisting of aspartic acid, glutamic acid, glutamine, asparagine and lysine or the N-substituted glycine residue of the formula (3); and m and n are 1, or a pharmacologically acceptable salt thereof.

4. The depsipeptide of the formula (2) as claimed in claim 1 wherein A is an N-($C_1$–$C_4$) alkylglycine residue of the formula (3); B is an N-($C_1$–$C_4$) alkylglycine residue of the formula (3); D is a residue of an amino acid selected from the group consisting of valine, phenylalanine, alanine and aspartic acid; E and F are each independently residues of an amino acid selected from the group consisting of leucine, isoleucine and alanine; W is a residue of an amino acid selected from the group consisting of aspartic acid, glutamic acid and the amino acid of the formula (4); Z is a residue of an amino acid selected from the group consisting of aspartic acid, glutamic acid, glutamine, asparagine and lysine or the N-substituted glycine residue of the formula (3); and m and n are 1, or a pharmacologically acceptable salt thereof.

5. A composition comprising the depsipeptide as claimed in claim 1 and a pharmaceutically acceptable carrier therefor.

6. A pharmaceutical composition for promoting the production of apolipoprotein E which contains as an active ingredient a therapeutically effective amount of the depsipeptide as claimed in claim 1 and a pharmaceutically acceptable carrier therefor.

7. A pharmaceutical composition for treating neurologic damages which contains as an active ingredient a therapeutically effective amount of the depsipeptide as claimed in claim 1 and a pharmaceutically acceptable carrier therefor.

8. A pharmaceutical composition for treating dementia which contains as an active ingredient a therapeutically effective amount of the depsipeptide as claimed in claim 1 and a pharmaceutically acceptable carrier therefor.

9. A pharmaceutical composition for treating hyperlipemia which contains as an active ingredient a therapeutically effective amount of the depsipeptide as claimed in claim 1 and a pharmaceutically acceptable carrier therefor.

* * * * *

```
                         SEQUENCE LISTING

<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<221> NAME/KEY: misc_feature
<223> OTHER INFORMATION: Descritpion of Artificial Sequence: synthetic
      peptide
<221> NAME/KEY: MOD_RES
<222> LOCATION: (1)..(1)
<223> OTHER INFORMATION: modified Val
<221> NAME/KEY: MOD_RES
<222> LOCATION: (2)..(2)
<223> OTHER INFORMATION: modified Asp
<221> NAME/KEY: MOD_RES
<222> LOCATION: (4)..(4)
<223> OTHER INFORMATION: modified Ile

<400> SEQUENCE: 1

Val Asp Leu Ile
1

<210> SEQ ID NO 2
<211> LENGTH: 6
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: MOD_RES
<222> LOCATION: (1)..(1)
<223> OTHER INFORMATION: modified Leu
<221> NAME/KEY: MOD_RES
<222> LOCATION: (2)..(2)
<223> OTHER INFORMATION: modified Gly
<221> NAME/KEY: MOD_RES
<222> LOCATION: (4)..(4)
<223> OTHER INFORMATION: modified Asp
<221> NAME/KEY: MOD_RES
<222> LOCATION: (6)..(6)
```

```
<223> OTHER INFORMATION: modified Ile

<400> SEQUENCE: 2

Leu Gly Val Asp Leu Ile
1               5

<210> SEQ ID NO 3
<211> LENGTH: 7
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: MOD_RES
<222> LOCATION: (1)..(1)
<223> OTHER INFORMATION: modified Gln
<221> NAME/KEY: MOD_RES
<222> LOCATION: (3)..(3)
<223> OTHER INFORMATION: modified Gly
<221> NAME/KEY: MOD_RES
<222> LOCATION: (5)..(5)
<223> OTHER INFORMATION: modified Asp
<221> NAME/KEY: MOD_RES
<222> LOCATION: (7)..(7)
<223> OTHER INFORMATION: modified Ile

<400> SEQUENCE: 3

Gln Leu Gly Val Asp Leu Ile
1               5

<210> SEQ ID NO 4
<211> LENGTH: 7
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: MOD_RES
<222> LOCATION: (1)..(1)
<223> OTHER INFORMATION: modified Gln
<221> NAME/KEY: MOD_RES
<222> LOCATION: (3)..(3)
<223> OTHER INFORMATION: modified Gly
<221> NAME/KEY: MOD_RES
<222> LOCATION: (5)..(5)
<223> OTHER INFORMATION: modified Asp
<221> NAME/KEY: MOD_RES
<222> LOCATION: (7)..(7)
<223> OTHER INFORMATION: modified Ile

<400> SEQUENCE: 4

Gln Leu Gly Val Asp Leu Ile
1               5

<210> SEQ ID NO 5
<211> LENGTH: 7
<212> TYPE: PRT
<213> ORGANISM: Artificial Sequence
<220> FEATURE:
<221> NAME/KEY: misc_feature
<223> OTHER INFORMATION: Description of Artificial Sequence: synthetic
      peptide
<221> NAME/KEY: MOD_RES
<222> LOCATION: (1)..(1)
<223> OTHER INFORMATION: modified Gln
<221> NAME/KEY: MOD_RES
<222> LOCATION: (3)..(3)
<223> OTHER INFORMATION: modified Gly
<221> NAME/KEY: MOD_RES
<222> LOCATION: (7)..(7)
<223> OTHER INFORMATION: modified Ile
```

```
<400> SEQUENCE: 5

Gln Leu Gly Val Asp Leu Ile
1               5
```